(12) United States Patent
Chang et al.

(10) Patent No.: US 12,023,435 B2
(45) Date of Patent: Jul. 2, 2024

(54) NEBULIZER

(71) Applicant: HCMed Innovations Co., LTD., Taipei (TW)

(72) Inventors: Chia-Chien Chang, New Taipei (TW); Chien-Shen Tsai, New Taipei (TW); Yuan-Ming Hsu, New Taipei (TW)

(73) Assignee: HCMed Innovations Co., LTD., Taipei (TW)

(*) Notice: Subject to any disclaimer, the term of this patent is extended or adjusted under 35 U.S.C. 154(b) by 659 days.

(21) Appl. No.: 17/349,893

(22) Filed: Jun. 16, 2021

(65) Prior Publication Data

US 2022/0249785 A1    Aug. 11, 2022

(30) Foreign Application Priority Data

Feb. 9, 2021    (TW) ................... 110104860

(51) Int. Cl.
    *A61M 11/00*    (2006.01)
    *A61M 15/00*    (2006.01)
(52) U.S. Cl.
    CPC ...... *A61M 11/005* (2013.01); *A61M 15/0021* (2014.02); *A61M 15/0065* (2013.01);
(Continued)
(58) Field of Classification Search
    CPC .......... A61M 15/0021; A61M 15/0023; A61M 15/0025; A61M 15/0026; A61M 15/0065; A61M 15/0066; A61M 2205/3327; A61M 2205/333; A61M 15/002; A61M 15/0005; A61M 15/001; A61M 15/0085; A61M 15/009; A61M 15/0091; A61M 15/0095;
(Continued)

(56) References Cited

U.S. PATENT DOCUMENTS

2019/0076605 A1    3/2019    Tsai et al.
2019/0240428 A1*    8/2019    Stenzler ............... A61M 11/001
(Continued)

FOREIGN PATENT DOCUMENTS

CN    105311719 A    2/2016
CN    205198624 U    5/2016
(Continued)

*Primary Examiner* — Kendra D Carter
*Assistant Examiner* — Jaeick Jang
(74) *Attorney, Agent, or Firm* — Li & Cai Intellectual Property Office

(57) ABSTRACT

A nebulizer including a host having a head portion, a cup body having a nebulizing module disposed on a bottom thereof, an engaging member, a mouthpiece having a first opening, a second opening, and a tongue plate, and a sensor element is provided. The engaging member includes a first, a second, and a third engaging opening communicated with one another. The cup body is coupled to the engaging member through the first engaging opening. The engaging member, inside which a first partition wall is disposed, is coupled to the host through having the third engaging opening engaged with the head portion. The mouthpiece is coupled to the engaging member through having the second opening engaged with the second engaging opening. The tongue plate, disposed inside the mouthpiece and abuts against the first partition wall, divides an inner space of the mouthpiece into a first and a second channel.

14 Claims, 14 Drawing Sheets

(52) U.S. Cl.
CPC . *A61M 15/0085* (2013.01); *A61M 2205/3327* (2013.01); *A61M 2205/3331* (2013.01)

(58) Field of Classification Search
CPC ............ A61M 11/005; A61M 2202/03; A61M 2202/04; A61M 16/0488; A61M 16/049; A61M 11/00
See application file for complete search history.

(56) References Cited

U.S. PATENT DOCUMENTS

| | | | |
|---|---|---|---|
| 2020/0030553 A1 | 1/2020 | Keip et al. | |
| 2021/0187214 A1* | 6/2021 | Marcoz | A61M 15/0071 |

FOREIGN PATENT DOCUMENTS

| | | | |
|---|---|---|---|
| CN | 206198413 U | | 5/2017 |
| CN | 108478910 A | | 9/2018 |
| CN | 109045425 A | | 12/2018 |
| CN | 208464864 U | | 2/2019 |
| CN | 109562236 A | | 4/2019 |
| CN | 110167618 A | | 8/2019 |
| EP | 3701987 A1 | | 9/2020 |
| TW | M603364 U | * | 11/2020 |
| TW | M603364 U | | 11/2020 |
| TW | M614315 U | * | 7/2021 |
| TW | M614315 U | | 7/2021 |

\* cited by examiner

NEBULIZER

CROSS-REFERENCE TO RELATED PATENT APPLICATION

This application claims the benefit of priority to Taiwan Patent Application No. 110104860, filed on Feb. 9, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a nebulizer, and more particularly to a nebulizer that detects a pressure change.

BACKGROUND OF THE DISCLOSURE

A conventional nebulizer continuously sprays medicinal liquid aerosols at a constant rate after being activated, but cannot automatically adapt an amount of nebulized volume according to a respiratory frequency, rate change, waveform change, and/or a lung capacity of a user, i.e., influences of individual differences on inhalation of medicines are not comprehensively taken into account. That is to say, even when the user is not inhaling, the nebulizer still continues to spray the medical liquid aerosols at the same constant rate, resulting in a decreased utilization rate of the medicine and/or discomfort of the user. In order to solve the above inadequacies, the conventional nebulizer uses a pressure detector to detect pressure changes caused by the user breathing through the nebulizer as an information basis for the nebulizer to be driven to produce the medicinal liquid aerosols. However, since the pressure detector is usually embedded inside the nebulizer, a structure of the nebulizer causes the nebulized gas (e.g., the medical liquid aerosols) to affect the accuracy of the pressure changes detected.

Therefore, it has become an important issue in the industry to prevent the nebulized gas from entering a pressure detection channel and consequentially affecting the sensitivity and accuracy of the pressure detector when detecting the respiration-generated pressure changes through a structural modification of the nebulizer.

SUMMARY OF THE DISCLOSURE

In response to the above-referenced technical inadequacies, the present disclosure provides a nebulizer.

In one aspect, the present disclosure provides a nebulizer including a host that includes a head portion, a cup body, an engaging member, a mouthpiece, and a sensor element. A nebulizing module is disposed on a bottom of the cup body. The engaging member includes a first engaging opening, a second engaging opening, and a third engaging opening that are communicated with one another. The cup body is coupled to the engaging member through the first engaging opening. The engaging member is coupled to the host through having the third engaging opening being engaged with the head portion. A first partition wall is placed in an inner space of the engaging member. The mouthpiece has a first opening and a second opening disposed corresponding to each other. The mouthpiece is coupled to the engaging member through having the second opening engaged with the second engaging opening. The mouthpiece includes a tongue plate. The tongue plate is disposed in an inner space of the mouthpiece and abuts against the first partition wall. The tongue plate divides the inner space of the mouthpiece into a first channel and a second channel. The sensor element is disposed in an inner space of the host. A horizontal distance between the sensor element and the first opening is smaller than a horizontal distance between the nebulizing module and the first opening.

One of the beneficial effects of the nebulizer of the present disclosure is that the nebulizer is able to prevent the nebulized gas from entering a pressure detection channel and affecting accuracy of the respiration-generated pressure detection, and to increase sensitivity of pressure detection through the technical solutions of "the tongue plate dividing the inner space of the mouthpiece into a first channel and a second channel which are respectively communicated with the cavity and the through hole" and "a horizontal distance between the sensor element and the first opening being smaller than a horizontal distance between the nebulizing module and the first opening".

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
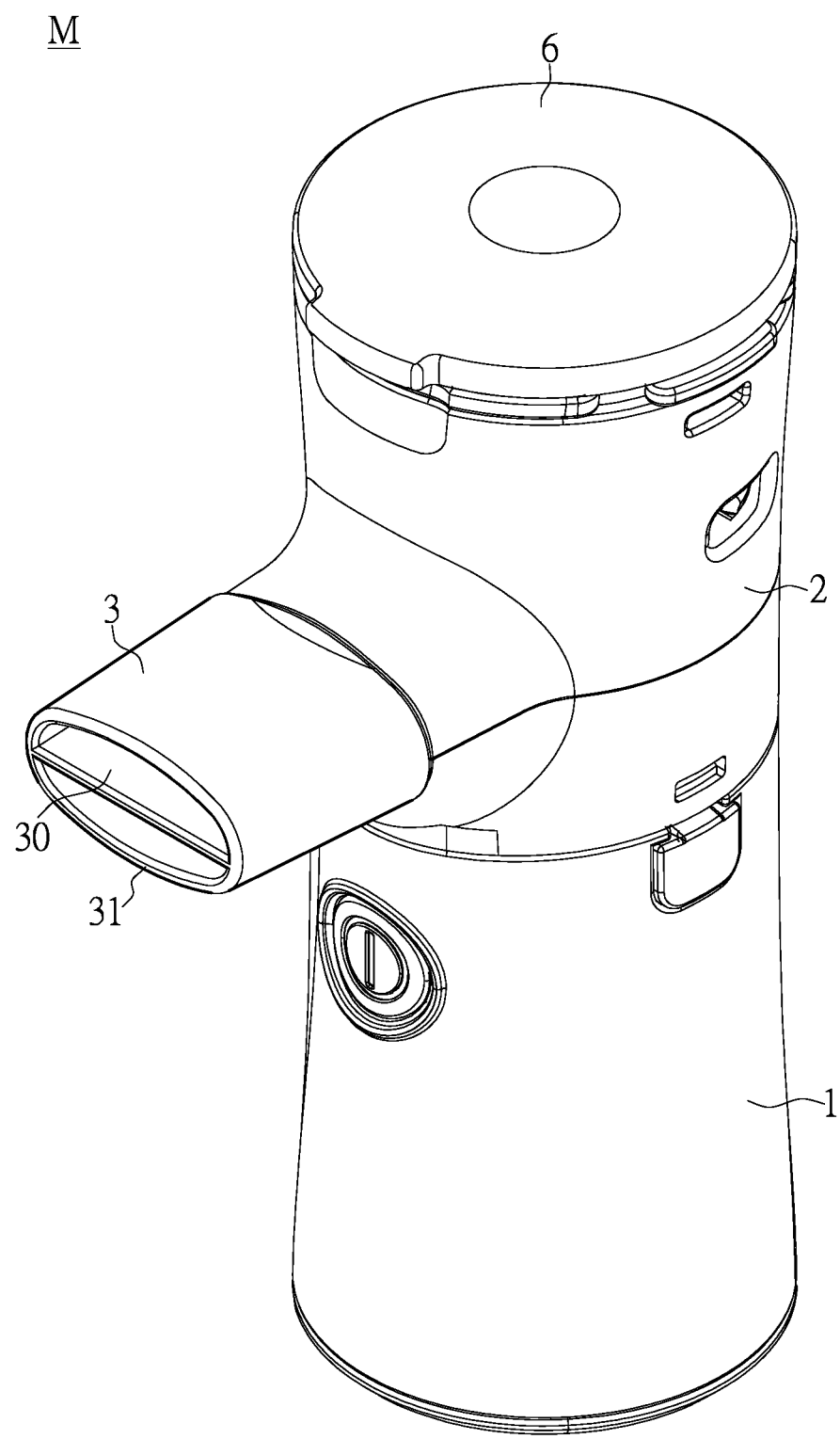
FIG. 1 is a first schematic perspective view of a nebulizer of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 2:
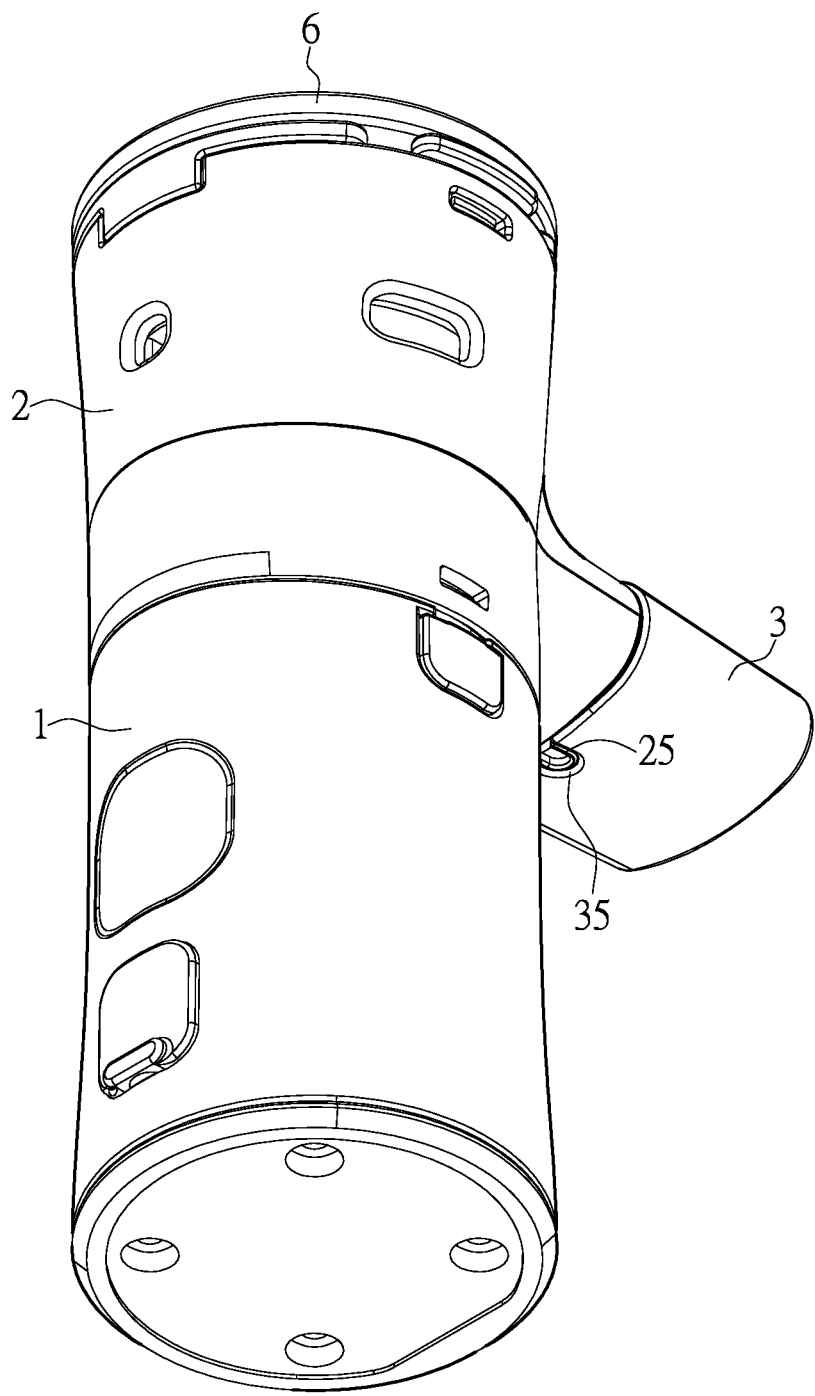
FIG. 2 is a second schematic perspective view of the nebulizer of the present disclosure.

Referring to FIG. 1 and FIG. 2, the present disclosure provides a nebulizer M. In terms of an appearance and a structure of the nebulizer M, the main structure of the nebulizer M includes a host 1, an engaging member 2, a mouthpiece 3, and a cup body 6. The mouthpiece 3 includes a first positioning portion 35. The engaging member 2 has a second positioning portion 25 corresponding to the first positioning portion 35 adjacent to a second engaging opening 212, and the mouthpiece 3 is engaged with the engaging member 2 through having the first positioning portion 35 fastened to the second positioning portion 25.

Figure 3:
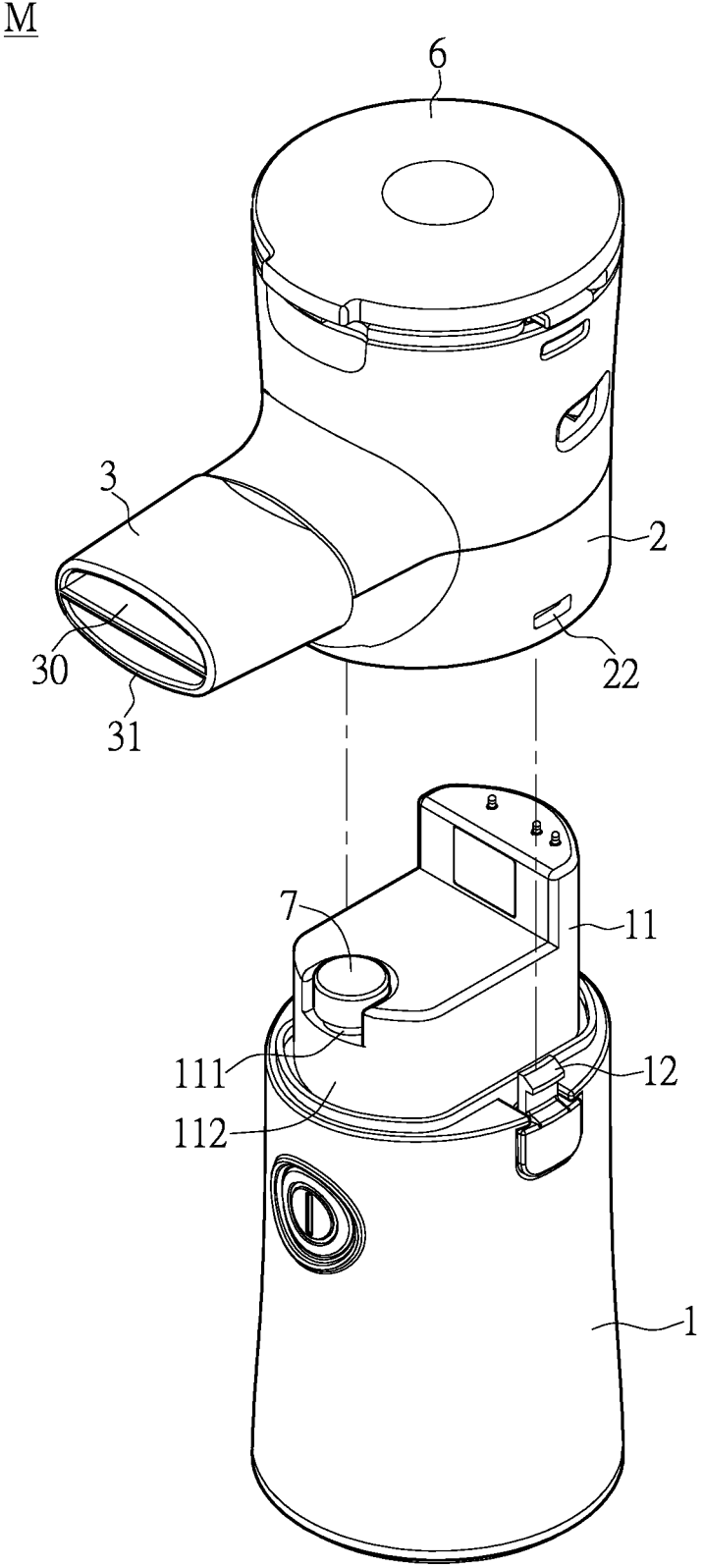
FIG. 3 is a first schematic exploded view of the nebulizer according to a first embodiment of the present disclosure.
Figure 4:
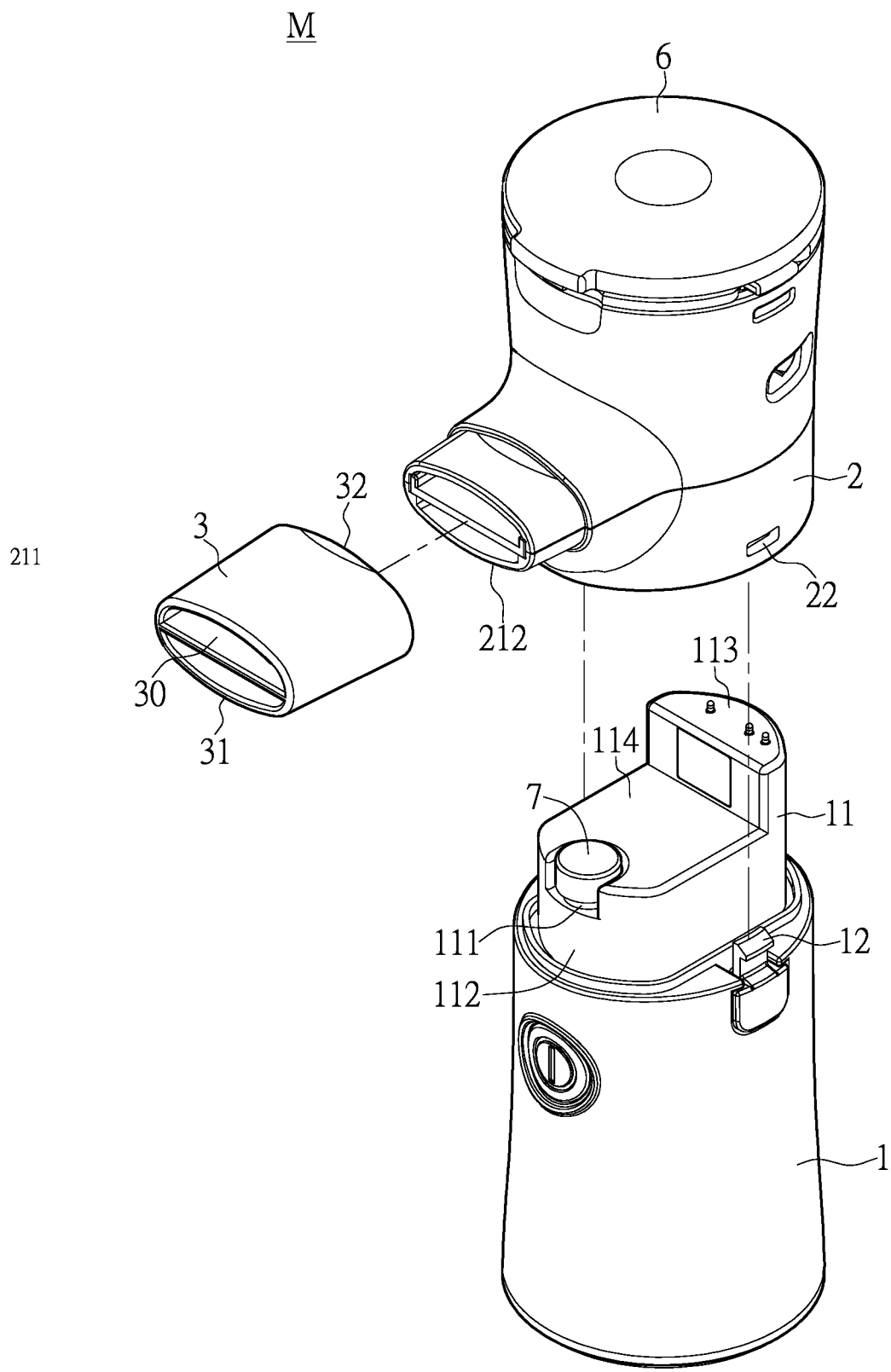
FIG. 4 is a second schematic exploded view of the nebulizer according to the first embodiment of the present disclosure.

Referring to FIG. 3 and FIG. 4, which are exploded schematic views of the nebulizer M. The host 1, the engaging member 2, and the mouthpiece 3 are components that can be disassembled and assembled, i.e., the host 1 and the engaging member 2 are joinable parts that can be engaged with each other, and the engaging member 2 and the mouthpiece 3 are joinable parts that can be engaged with each other. However, the above-mentioned example is only one of the feasible embodiments, and is not meant to limit the present disclosure. For example, in another embodiment, the engaging member 2 and the mouthpiece 3 can also be an integrally formed component. Furthermore, the host 1 has a head portion 11. The head portion 11 has a through hole 111, and the through hole 111 is formed on an upper surface of the head portion 11. More specifically, the head portion 11 of the host 1 is substantially in a stepped shape protruding structure, which includes a high platform surface 113 and a low platform surface 114. The low platform surface 114 is disposed between the through hole 111 and the high platform surface 113.

Further referring to FIG. 4, a first fastening member 22 is disposed on each of two sides of the engaging member 2. A second fastening member 12 corresponding to the first fastening member 22 is disposed on each of two sides of the host 1. When the engaging member 2 is coupled to the host 1, the first fastening member 22 is fastened to the second fastening member 12. In the present disclosure, the first fastening member 22 is a buckle hole, and the second fastening member 12 is a hook, but the present disclosure is not limited thereto.

Figure 5:
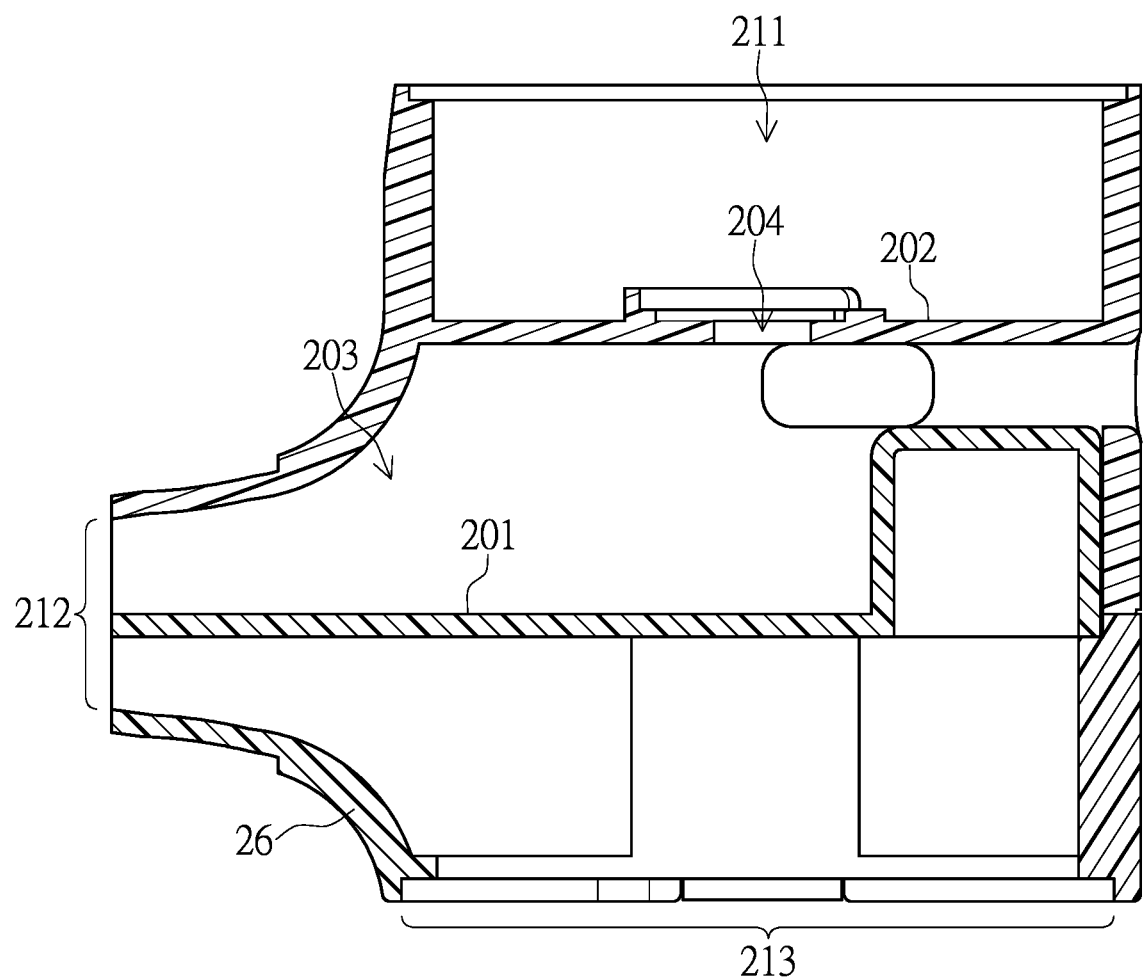
FIG. 5 is a schematic view of an engaging member of the nebulizer according to the first embodiment of the present disclosure.

Referring to FIG. 5, which is a schematic view of an engaging member of the nebulizer according to the first embodiment of the present disclosure. The engaging member 2 includes a first engaging opening 211, a second engaging opening 212, and a third engaging opening 213 that are communicated with one another, and a first partition wall 201 is disposed in an inner space of the engaging member 2. A side wall 26 is positioned between the second engaging opening 212 and the third engaging opening 213. The nebulizer M further includes a second partition wall 202, and the second partition wall 202 and the engaging member 2 are integrally formed. A cavity 203 is divided from the inner space of the engaging member 2 by the second partition wall 202 and the first partition wall 201. The second partition wall 202 has a second penetrating hole 204, the first engaging opening 211 is communicated with the cavity 203 through the second penetrating hole 204, and the second engaging opening 212 is also communicated with the cavity 203.

Figure 6:
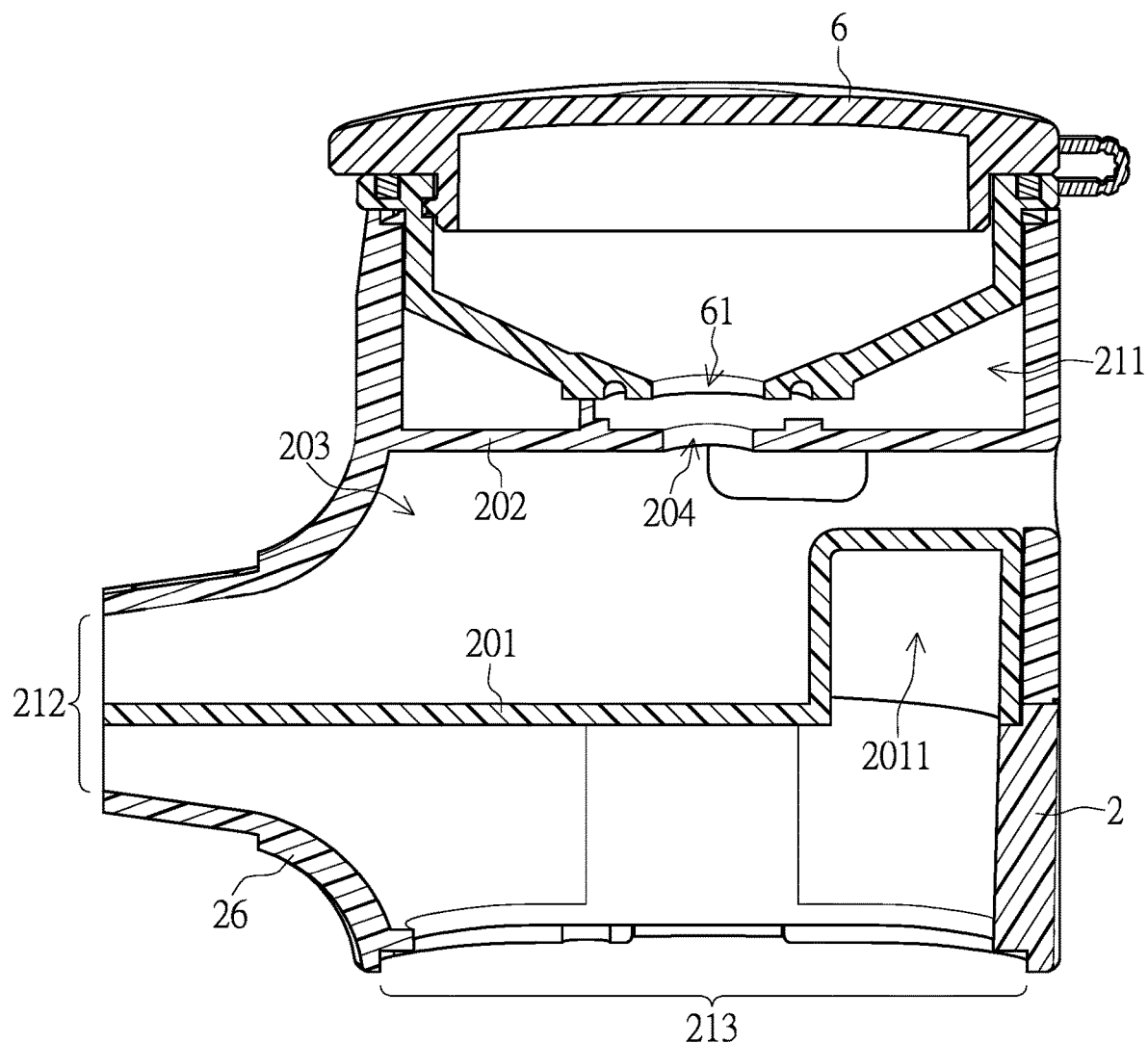
FIG. 6 is a schematic cross-sectional view showing the engaging member and a cup body of the nebulizer being assembled according to the first embodiment of the present disclosure.

FIG. 6 is a schematic cross-sectional view showing the engaging member and a cup body of the nebulizer being assembled according to the first embodiment of the present disclosure. In addition, an assembly of the cup body 6 and the engaging member 2 is shown in FIG. 4. When the cup body 6 is assembled with the engaging member 2, the cup body 6 is disposed on the first engaging opening 211, and meanwhile, a first penetrating hole 61 and the second penetrating hole 204 are disposed oppositely. Furthermore, the first partition wall 201 is in a stepped shape, the first partition wall 201 has an accommodating portion 2011 positioned relative to a side of the cavity 203, and a shape of the accommodating portion 2011 corresponds to the high platform surface 113.

Figure 7:
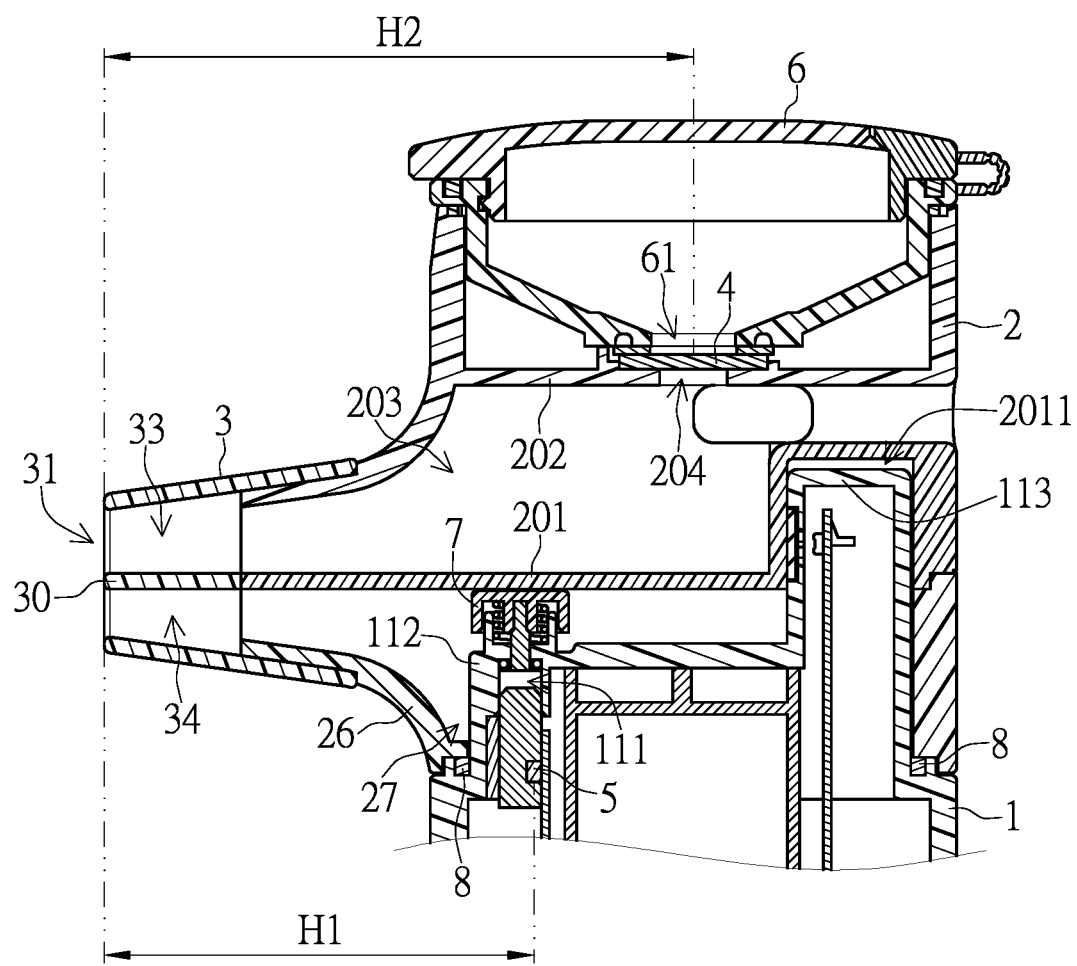
FIG. 7 is a schematic cross-sectional view of the nebulizer according to the first embodiment of the present disclosure.

FIG. 7 is a schematic cross-sectional view of the nebulizer according to the first embodiment of the present disclosure. In addition, an assembly of the engaging member 2 and the host 1 is shown in FIG. 4. The engaging member 2 is coupled to the host 1 through having the third engaging opening 213 being coupled to the head portion 11, and the high platform surface 113 is positioned in the accommodating portion 2011. The mouthpiece 3 has a first opening 31 and a second opening 32 corresponding to each other. The mouthpiece 3 is connected to the second engaging opening 212 through having the second opening 32 coupled to the engaging member 2. As shown in FIG. 7, the nebulizer M of the present disclosure further includes a nebulizing module 4 and a sensor element 5. The nebulizing module 4 is disposed above the second penetrating hole 204, and the sensor element 5 is disposed inside the host 1. The first penetrating hole 61 is formed on a bottom of the cup body 6, and the first penetrating hole 61 is positioned above the nebulizing module 4. In other words, the nebulizing module 4 is disposed between the first penetrating hole 61 and the second penetrating hole 204.

Liquid medicine can be arranged inside the cup body 6 and pass through the first penetrating hole 61, such that the liquid medicine is converted into aerosols by the nebulizing module 4, and then the aerosols are dispersed in the cavity 203 through the second penetrating hole 204. It is worth mentioning that a horizontal arrangement of the nebulizing module 4 enables the aerosols converted by the nebulizing module 4 to be dispersed in the cavity 203, instead of being directly sprayed towards the first opening 31. In addition, when the engaging member 2 is coupled to the host 1, a groove 27 is formed between the side wall 26 of the engaging member 2 and a side surface 112 of the head portion 11. In addition, the nebulizer M of the present disclosure further includes a sealing ring 8 which is arranged around the head portion 11 of the host 1. When the engaging member 2 is coupled to the host 1, the sealing ring 8 is positioned at a joint between the engaging member 2 and the host 1.

Reference is further made to FIG. 7, and the mouthpiece 3 includes a tongue plate 30 which is arranged inside the mouthpiece 3 and abuts against the first partition wall 201. The tongue plate 30 divides an inner space of the mouthpiece 3 into a first channel 33 and a second channel 34 that are independent from each other. The first channel 33 is communicated with the cavity 203, and the second channel 34 is communicated with an inner space of the host 1 through the second engaging opening 212 and the through hole 111. The through hole 111 is communicated with the inner space of the host 1 and the second channel 34, such that the sensor element 5 disposed inside the host 1 can sense a pressure change of the second channel 34. Furthermore, a horizontal distance H1 between the sensor element 5 and the first opening 31 is smaller than a horizontal distance H2 between the nebulizing module 4 and the first opening 31. More specifically, the horizontal distance H1 is a distance between the sensor element 5 and an end edge of the mouthpiece 3 for forming the first opening 31, and the horizontal distance H2 is a distance between the nebulizing module 4 and the end edge of the mouthpiece 3 for forming the first opening 31. In addition, the nebulizer M further includes a waterproof component 7, which is sheathed on the through hole 111 and completely covers a detection area of the sensor element 5. The sensor element 5 is vertically disposed in the inner space of the host 1, according to an orientation of the through hole 111. The waterproof component 7 is able to block water vapor and prevent the water vapor from entering the inner space of the host 1 from the through hole 111 and affecting the functionality of circuits and electronic components inside the host 1.

Figure 8:
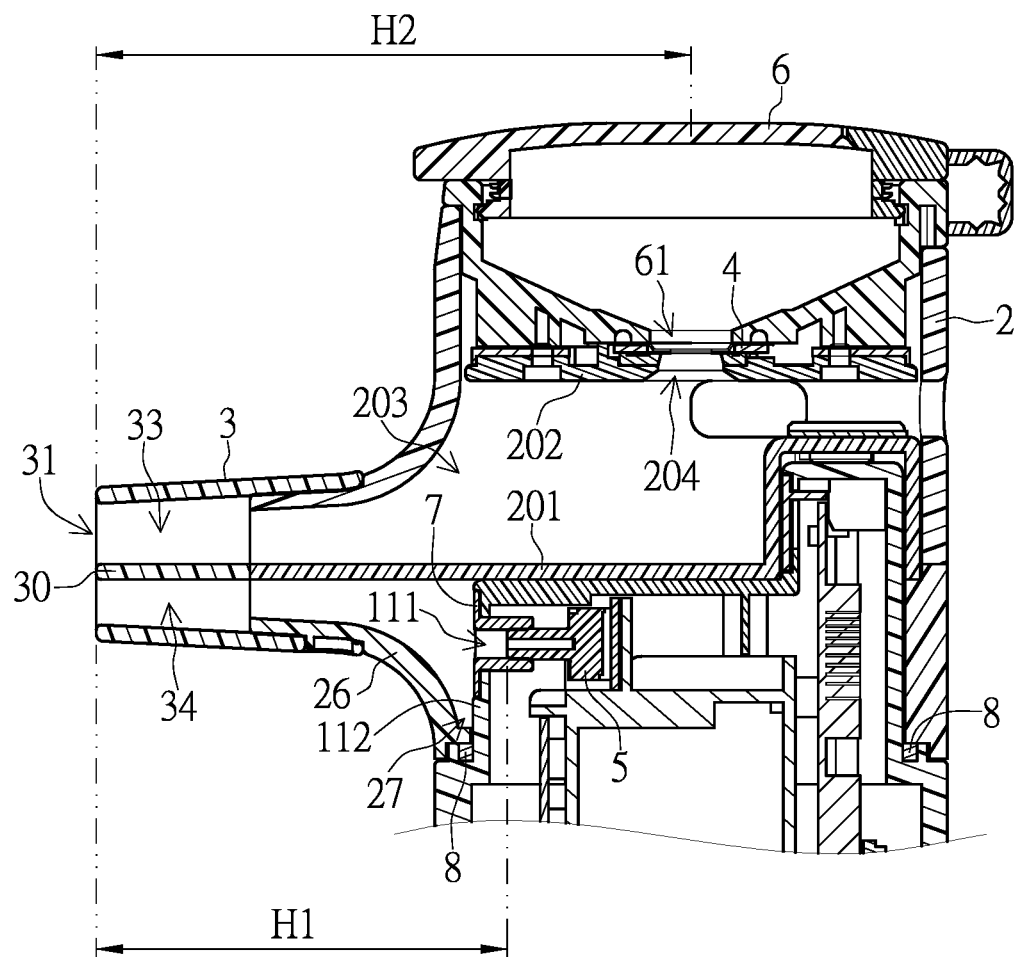
FIG. 8 is a schematic cross-sectional view of another implementation of the nebulizer according to the first embodiment of the present disclosure.

It is worth mentioning that, although the second partition wall 202 and the engaging member 2 are integrally formed in this embodiment, the present disclosure is not limited thereto. In other embodiments, referring to FIG. 8, the second partition wall 202 can also be an independent element, and can be detachably arranged at the bottom of the cup body 6 or detachably arranged in the inner space of the engaging member 2.

Figure 9:
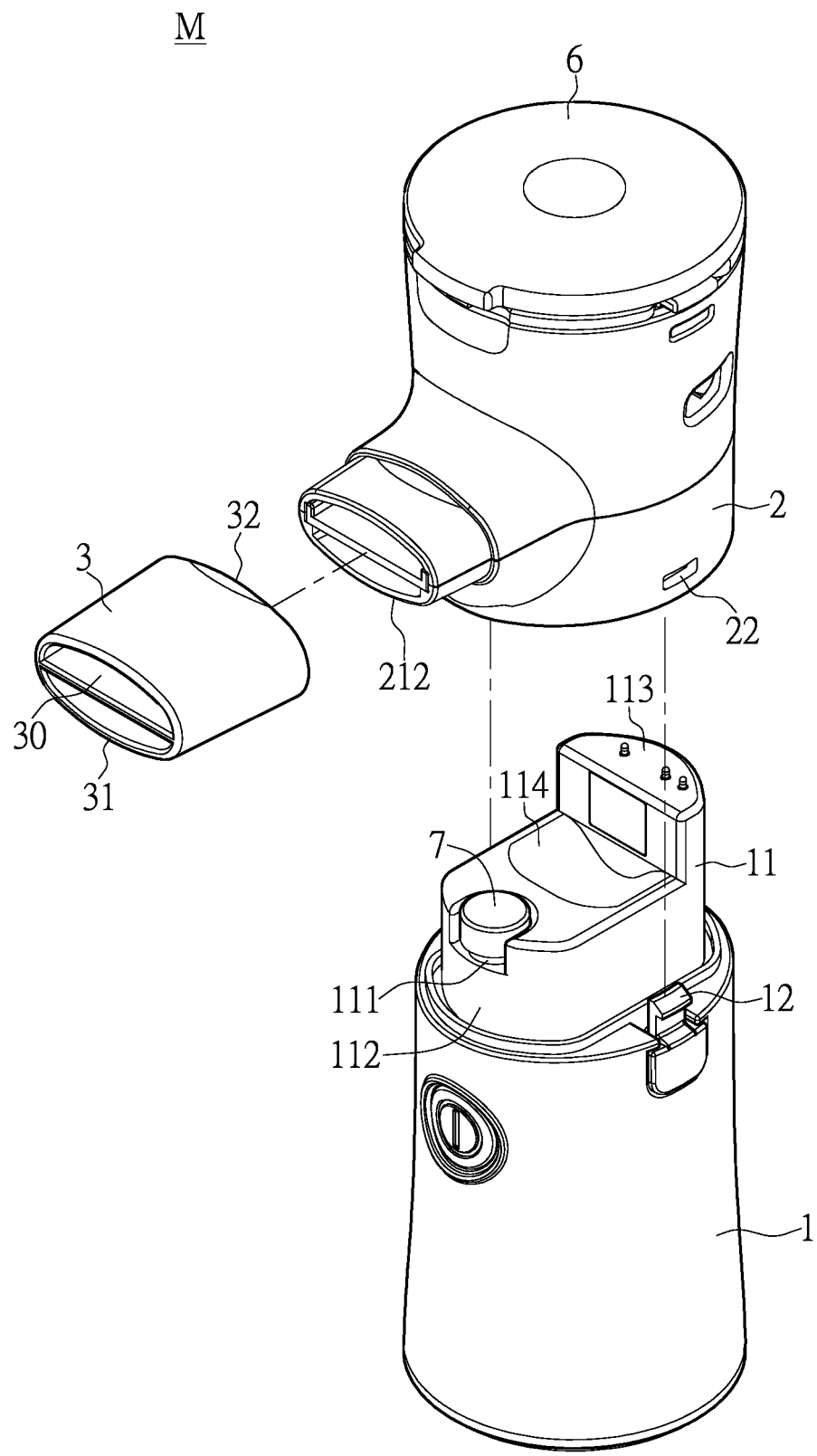
FIG. 9 is a schematic exploded view of yet another implementation of the nebulizer according to the first embodiment of the present disclosure.
Figure 10:
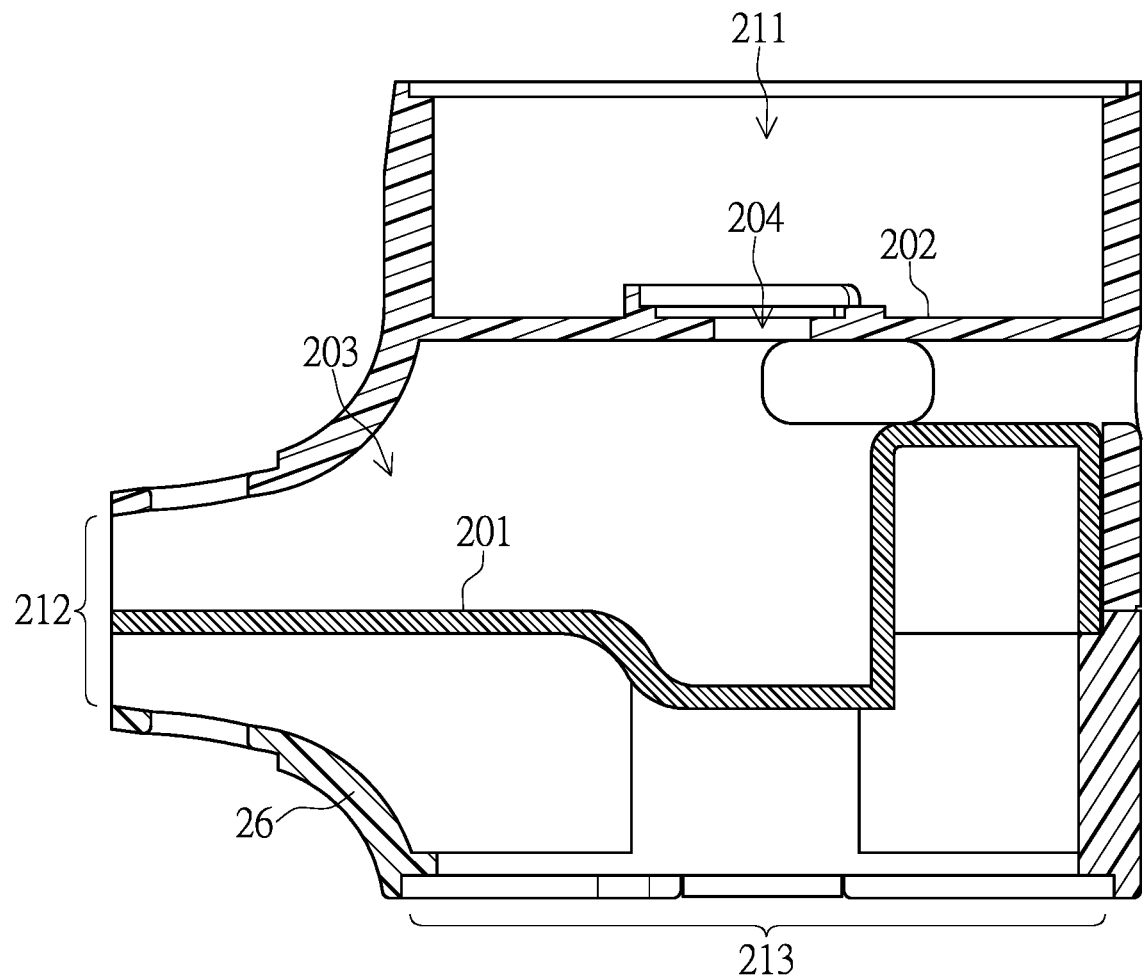
FIG. 10 is a schematic cross-sectional view of yet another implementation of the nebulizer according to the first embodiment of the present disclosure.

In addition, the head portion 11 of the host 1 of the nebulizer M can have a variety of implementations. Referring to FIG. 9 and FIG. 10, the low platform surface 114 of the head portion 11 between the high platform surface 113 and the through hole 111 can be a concave surface, and the first partition wall 201 of the engaging member 2 can have a sink groove. In a structural design of the sink groove, a distance between the first partition wall 201 and the nebulizing module 4 is elongated, so as to make a space of the cavity 203 larger. When the nebulizing module 4 converts the medicinal liquid into aerosols, the aerosols are dispersed in the cavity 203 through the second penetrating hole 204, such that the distance between the first partition wall 201 and the nebulizing module 4 is elongated, and a time for the aerosols to condense into liquid droplets to contact the first partition wall 201 is extended, which allows the user to inhale more of the aerosols.

Second Embodiment

Figure 11:
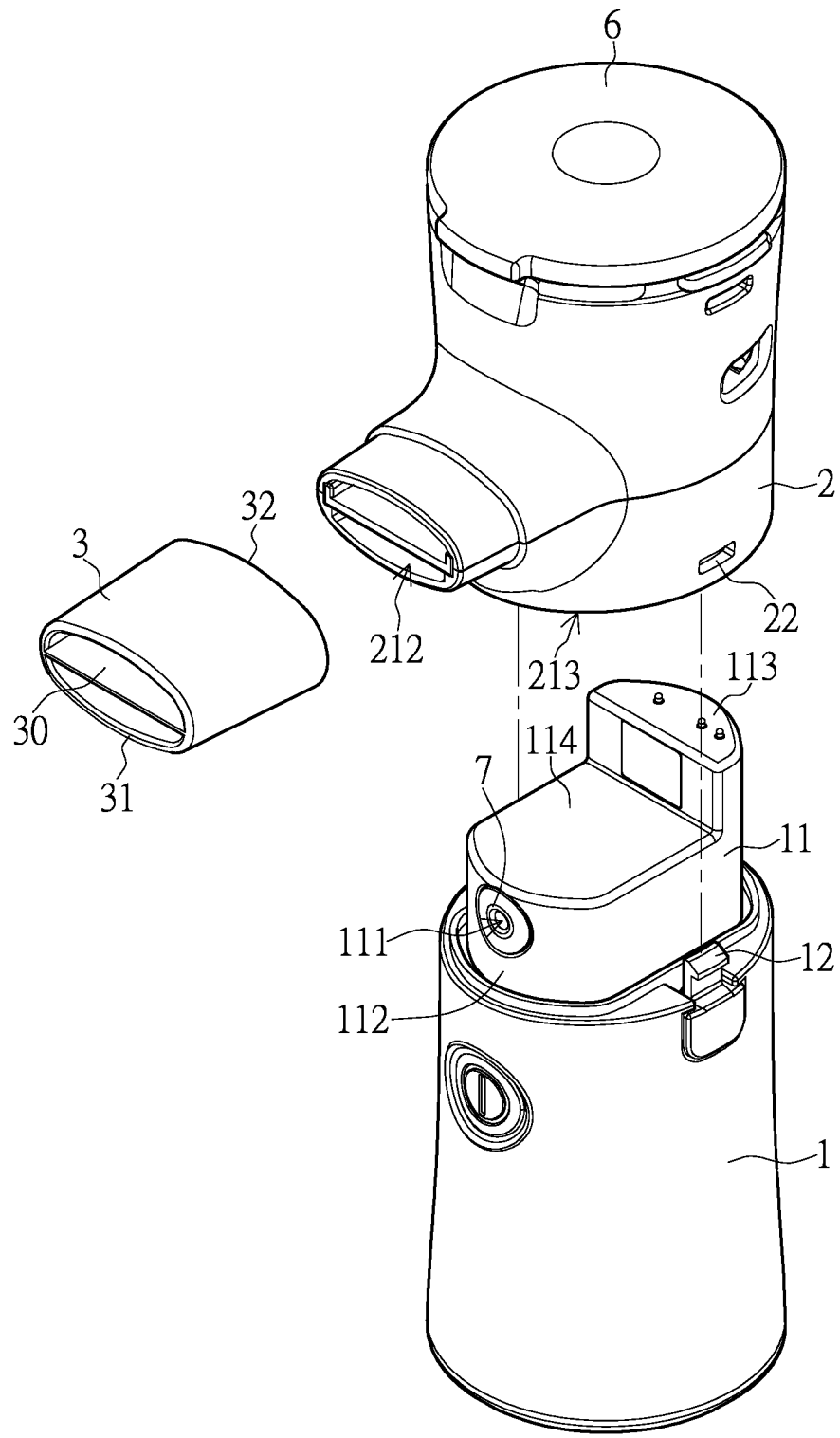
FIG. 11 is a schematic exploded view of the nebulizer according to a second embodiment of the present disclosure.
Figure 12:
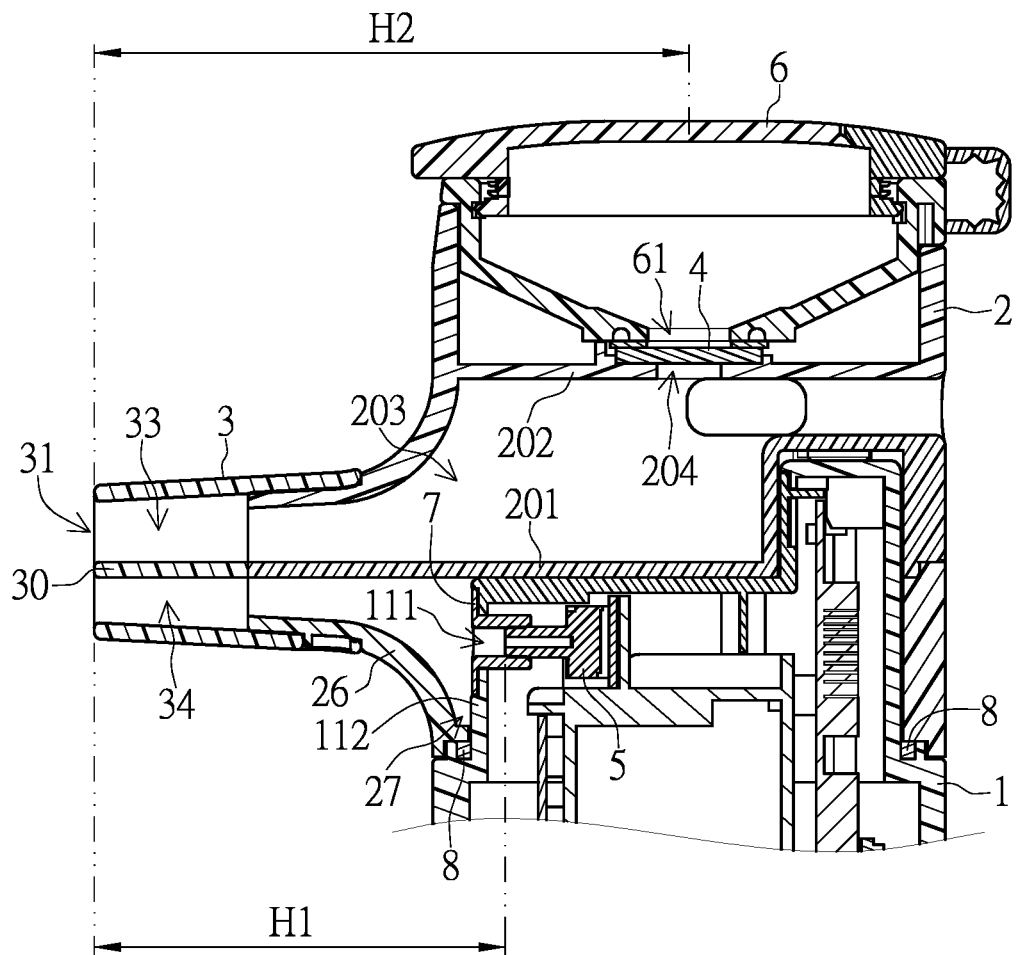
FIG. 12 is a schematic cross-sectional view of the nebulizer according to the second embodiment of the present disclosure.

Referring to FIG. 11 and FIG. 12, the nebulizer M in the second embodiment is mostly the same or similar in structure and function to the nebulizer M in the first embodiment, and the same or similar structure and function will not be reiterated herein. Compared with the first embodiment, the main difference between the nebulizer M in the second embodiment and that in the first embodiment of the present disclosure is that an outlet direction of the through hole 111 of the host 1 is different. More specifically, the through hole 111 in this embodiment is opened on the side surface 112 of the head portion 11, and the outlet direction thereof extends forward toward the first opening 31. In the first embodiment (as shown in FIG. 4), the through hole 111 is formed on the upper surface of the head portion 11, and the outlet direction thereof extends upward toward the first partition wall 201.

Similarly, the nebulizer M in this embodiment further includes the waterproof component 7, which is sheathed on the through hole 111 and exposes a part of the through hole 111 and the detection area of the sensor element 5, and the waterproof component 7 has the same function of blocking water vapor as that of the first embodiment. It is worth mentioning that the sensor element 5 shown in the nebulizer M in the second embodiment is waterproof to a certain extent. Therefore, the detection area of the sensor element 5 can be exposed from the waterproof assembly 7, and the sensor element 5 is arranged in the host 1 in a horizontal direction corresponding to the orientation of the through hole 111. Therefore, comparing with the first embodiment, the sensor element 5 in the second embodiment can detect the pressure change of the second channel 34 with higher sensitivity, i.e., the sensor element 5 in the second embodiment has better sensitivity. However, the above-mentioned example is only one of the feasible embodiments, and is not meant to limit the present disclosure. The nebulizer M of the present disclosure is not limited to structural designs of the sensor element 5 and the waterproof assembly 7.

Figure 13:
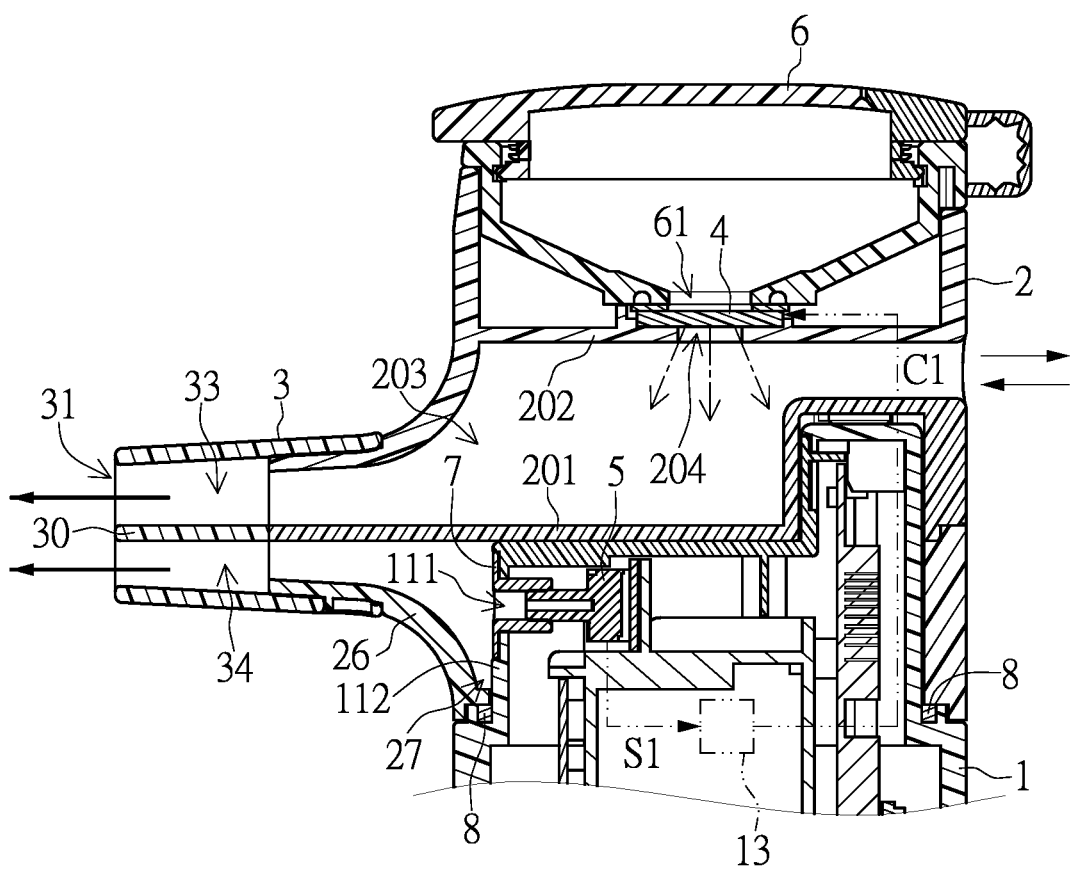
FIG. 13 is a schematic view showing an operation of the nebulizer during an inhalation process according to the second embodiment of the present disclosure.
Figure 14:
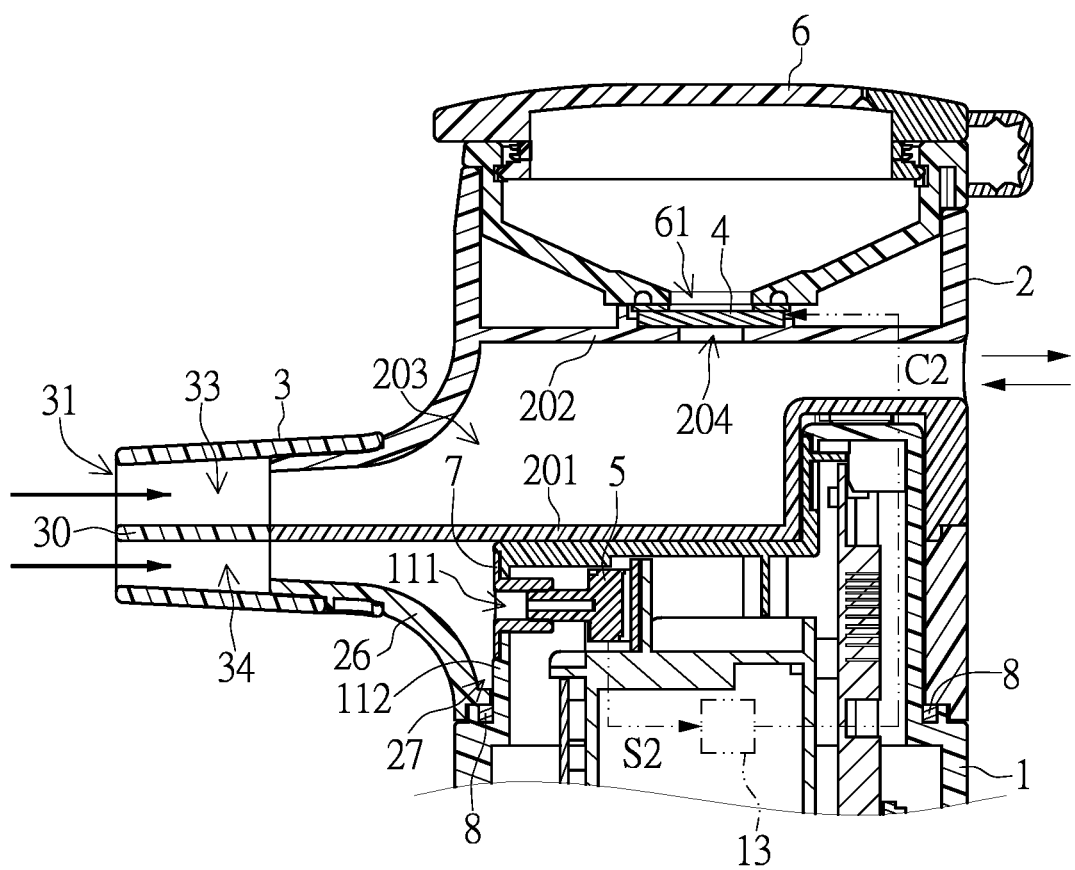
FIG. 14 is a schematic view showing an operation of the nebulizer during an exhalation process according to the second embodiment of the present disclosure.

Next, references are made to FIG. 13 and FIG. 14. FIG. 13 is a schematic view showing an operation of the nebulizer during an inhalation process according to the second embodiment of the present disclosure. FIG. 14 is a schematic view showing an operation of the nebulizer during an exhalation process according to the second embodiment of the present disclosure. It should be noted that although the operation of the nebulizer M of the present disclosure is illustrated by the structure of the nebulizer M shown in this embodiment (i.e., the second embodiment), the above-mentioned examples are only one of the feasible embodiments, and is not meant to limit the present disclosure. In fact, the operation of the nebulizer M of the present disclosure is also applicable to the structure of the nebulizer M shown in the first embodiment, which is described first herein.

As shown in FIG. 13, the sensor element 5 is electrically connected to the nebulizing module 4, and the host 1 further includes a control unit 13. When the user inhales from the first opening 31 (directions indicated by arrows at the first opening 31 are inhalation directions), the sensor element 5 outputs a first detection signal S1 through detecting the pressure change of the second channel 34 to the control unit 13. The control unit 13 outputs a first control signal C1 to the nebulizing module 4 according to the first detection signal S1. The nebulizing module 4 then converts the liquid medicine into aerosols triggered by the first control signal C1, and the aerosols are dispersed in the cavity 203 through the second penetrating hole 204. Afterwards, the aerosols pass through the first channel 33 and the first opening 31 to be inhaled into the respiratory tract of the user.

As shown in FIG. 14, when the user exhales into the first opening 31, the sensor element 5 outputs the second detection signal S2 to the control unit 13 through detecting the pressure change of the second channel 34. The control unit 13 outputs a second control signal C2 to the nebulizing module 4 according to the second detection signal S2. The nebulizing module 4 then stops converting the liquid medicine into the aerosol according to the second control signal C2.

Beneficial Effects of the Embodiments

One of the beneficial effects of the nebulizer M of the present disclosure is that the nebulizer M is able to prevent the nebulized gas from entering the pressure detection channel and affecting the accuracy of the detected respiratory (e.g., the inhalation and the exhalation of the user) pressure changes, and to increase the sensitivity of pressure detection through the technical solutions of "the tongue plate 30 dividing the inner space of the mouthpiece 3 into a first channel 33 and a second channel 34 which are respectively communicated with the cavity 203 and the through hole 111" and "the horizontal distance H1 between the sensor element 5 and the first opening 31 being smaller than the horizontal distance H2 between the nebulizing module 4 and the first opening 31".

Furthermore, as shown in FIG. 13 and FIG. 14, when the user inhales from or exhales into the first opening 31, the liquid vapor condenses in the second channel 34. The condensed liquid vapor can be naturally accumulated in the groove 27 through a structural design thereof, and the condensed liquid vapor can be prevented from flowing into the through hole 111.

Furthermore, since the horizontal distance H1 between the sensor element 5 and the first opening 31 is smaller than the horizontal distance H2 between the nebulizing module 4 and the first opening 31, compared to the nebulizing module 4, the sensor element 5 is closer to the first opening 31, i.e., closer to a mouth of the user. When the sensor element 5 is arranged closer to the first opening 31, the sensor element 5 can detect the pressure change with higher sensitivity, which indicates that the sensitivity of the sensor element 5 is increased.

Furthermore, in the structural design of the nebulizer M of the present disclosure, when the mouthpiece 3 is engaged with the engaging member 2, the tongue plate 30 and the first partition wall 201 can be accurately engaged to each other. The tongue plate 30 divides the inner space of the mouthpiece 3 into the first channel 33 and the second channel 34 that are independently separated from each other. The first channel 33 is communicated with the cavity 203, and the second channel 34 is communicated with the inner space of the host 1 through the through hole 111. The through hole 111 is communicated with the inner space of the host 1 and the second channel 34. Furthermore, the sensor element 5 is arranged in the through hole 111, so as to detect the pressure change of the second channel 34. In other words, the first channel 33 and the cavity 203 together form an aerosol channel, and the second channel 34 and the through hole 111 form the pressure detection channel. The aerosol channel and the pressure detection channel are independently separated from each other to prevent the aerosols formed by the liquid medicine from entering the pressure detection channel, such that an airflow of the aerosol is prevented from interfering with a determination of the pressure detection of the sensor element 5 when the user inhales from and exhales into the first opening 31.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A nebulizer, comprising:
   a host having a head portion;
   a cup body, a nebulizing module being disposed on a bottom of the cup body;
   an engaging member including a first engaging opening, a second engaging opening, and a third engaging opening that are communicated with one another, wherein the cup body is coupled to the engaging member through the first engaging opening, the engaging member is coupled to the host through having the third engaging opening being engaged with the head portion, and a first partition wall is disposed in an inner space of the engaging member;
   a mouthpiece having a first opening and a second opening disposed corresponding to each other, the mouthpiece being coupled to the engaging member through having the second opening being engaged with the second engaging opening, wherein the mouthpiece further includes a tongue plate, the tongue plate is disposed in an inner space of the mouthpiece and abuts against the first partition wall, and the tongue plate divides the inner space of the mouthpiece into a first channel and a second channel; and
   a sensor element disposed in an inner space of the host, a horizontal distance between the sensor element and the first opening being smaller than a horizontal distance between the nebulizing module and the first opening.

2. The nebulizer according to claim 1, further comprising a second partition wall, the second partition wall being detachably arranged at the bottom of the cup body, and a cavity being divided from the inner space of the engaging member by the second partition wall and the first partition wall, wherein the first channel is communicated with the cavity, a through hole is formed on the head portion, and the second channel is communicated with the inner space of the host through the through hole and the second engaging opening.

3. The nebulizer according to claim 2, wherein the second partition wall is detachably arranged in the inner space of the engaging member.

4. The nebulizer according to claim 1, wherein a first fastening member is disposed on each of two sides of the engaging member, and a second fastening member is disposed on each of two sides of the host corresponding to the first fastening members, respectively, and wherein, when the engaging member is coupled to the host, the first fastening member is fastened to the second fastening member.

5. The nebulizer according to claim 1, wherein a through hole is formed on the head portion, the through hole is communicated with the inner space of the host and the second channel, and the sensor element is communicated with the second channel through the through hole to detect a pressure change of the second channel.

6. The nebulizer according to claim 5, further comprising a waterproof component, the waterproof component being sheathed on the through hole.

7. The nebulizer according to claim 5, wherein the through hole is formed on an upper surface of the head portion.

8. The nebulizer according to claim 5, wherein the through hole is formed on a side surface of the head portion.

9. The nebulizer according to claim 1, wherein the sensor element is electrically connected to the nebulizing module, and the host further includes a control unit, and wherein, when a user inhales from the first opening, the sensor element outputs a first detection signal to the control unit according to the pressure change detected from the second channel, and the control unit outputs a first control signal to the nebulizing module according to the first detection signal.

10. The nebulizer according to claim 9, wherein, when the user exhales into the first opening, the sensor element outputs a second detection signal to the control unit according to the pressure change detected from the second channel, and the control unit outputs a second control signal to the nebulizing module according to the second detection signal.

11. The nebulizer according to claim 5, wherein the head portion includes a high platform surface, and a low platform surface, and the low platform surface is disposed between the through hole and the high platform surface.

12. The nebulizer according to claim 11, wherein the low platform surface is a concave surface.

13. The nebulizer according to claim 1, wherein the first partition wall has a sink groove.

14. The nebulizer according to claim 1, wherein a groove is formed between a side wall between the second engaging opening and the third engaging opening and a side surface of the head portion by the engaging member.

* * * * *